(12) United States Patent
Rosenblatt

(10) Patent No.: US 6,912,416 B2
(45) Date of Patent: Jun. 28, 2005

(54) DETECTING OR PREVENTING TISSUE DAMAGE

(76) Inventor: Peter L. Rosenblatt, 25 Bruce La., Newton, MA (US) 02458

( * ) Notice: Subject to any disclaimer, the term of this patent is extended or adjusted under 35 U.S.C. 154(b) by 228 days.

(21) Appl. No.: 10/198,592

(22) Filed: Jul. 18, 2002

(65) Prior Publication Data

US 2003/0018279 A1 Jan. 23, 2003

Related U.S. Application Data

(60) Provisional application No. 60/306,077, filed on Jul. 18, 2001.

(51) Int. Cl.$^7$ ................................................ A61B 5/05
(52) U.S. Cl. ..................................................... 600/547
(58) Field of Search .......................... 600/547, 29, 30; 606/185, 41; 604/164.08, 264

(56) References Cited

U.S. PATENT DOCUMENTS

| | | | |
|---|---|---|---|
| 4,804,054 A | 2/1989 | Howson et al. ............. | 128/898 |
| 5,429,636 A | 7/1995 | Shikhman et al. ............ | 606/41 |
| 5,923,259 A | 7/1999 | Lederer ....................... | 340/605 |
| 2002/0147382 A1 * | 10/2002 | Neisz et al. .................. | 600/29 |

FOREIGN PATENT DOCUMENTS

EP        0 275 617 A1    1/1987

OTHER PUBLICATIONS

U. Ulmsten, C. Falconer, P. Johnson, M. Jomaa, L. Lanner, C.G. Nilsson and I. Olsson (1998), "A Multicenter Study of Tension–Free Vaginal Tape (TVT) for Surgical Treatment of Stress Urinary Incontinence", *International Urogynecology Journal* 9:210–213.
Product Brochure for Sparc ™ Sling System (2 pages).
Product Brochure for TVT Tension–free Vaginal Tape (2 pages).
International Search Report, PCT Pub. No. 02/22764, filed Jul. 18, 2002.

* cited by examiner

*Primary Examiner*—Max F. Hindenburg
*Assistant Examiner*—Brian Szmal
(74) *Attorney, Agent, or Firm*—Foley Hoag LLP; Scott E. Kamholz

(57) ABSTRACT

Systems and methods are described for, among other things, detecting tissue injury and for evaluating the integrity of an anatomic structure. A system may include a first sensor disposable through a first space on a first side of the anatomic structure, a second sensor disposed in a second space on a second side of the anatomic structure, and a processor coupled to the first sensor and to the second sensor, the processor including a meter, the meter responsive to a communication between the first sensor and the second sensor, wherein an invasion of the anatomic structure by the first sensor alters the communication between the first sensor and the second sensor.

34 Claims, 6 Drawing Sheets

DETECTING OR PREVENTING TISSUE DAMAGE

CROSS-REFERENCE TO RELATED APPLICATION

This application claims the benefit of priority to U.S. Provisional Patent Application Ser. No. 60/306,077, filed Jul. 18, 2001, which is incorporated herein in its entirety by this reference.

FIELD

The disclosed systems and methods relate generally to detecting and/or preventing tissue damage, including intraoperative tissue injury.

BACKGROUND

A wide variety of processes involve the employment of devices in close proximity to fragile or easily damaged or injured structures. Many medical and/or surgical procedures fall into this classification. For example, it is a common occurrence during surgery to contact unintentionally a structure other than intended. Such contact could result in or contribute to injury or damage to the contacted structure. This injury or damage may decrease the likelihood of success of a procedure, increase a patient's chance of death or continued illness, cause pain, delay recovery, prolong the duration of a procedure, and/or other undesirable results.

One particular example is bladder injury that may occur with antiincontinence and/or other surgery, and especially when needles are used to pass sutures and/or sling material from the vagina to the suprapubic region, or vice versa. In the popular Tension-free Vaginal Tape (TVT) procedure, inadvertent bladder injury may occur. This type of injury can be minor but could also result in some or all of the serious sequelae enumerated above. The chances of minimizing the injury are improved if the injury is recognized intraoperatively, so that the needle can be replaced in a slightly more lateral position. Repositioning typically requires intraoperative cystoscopy after filling the bladder with a sufficient amount of distention fluid, usually 300 cc of water or normal saline. Failure to visualize the bladder carefully or to fill the bladder sufficiently may lead to failure to recognize a bladder injury, which may result from placing needles, suture or sling material intravesically (in the bladder). This may lead to recurrent urinary tract infections, hematuria or stone formation. In addition, some qualified gynecologic surgeons do not have cystoscopy privileges at their hospitals, which prevent them from performing these procedures.

The art would be enhanced by the provision of systems and methods to help prevent and detect damage to tissues. In particular, the art would be enhanced by the provision of systems and methods that facilitate non-cystoscopic evaluation of bladder injury during antiincontinence surgery.

SUMMARY

Disclosed herein are systems and methods for detecting or preventing tissue injury and/or for evaluating the integrity of an anatomic structure. Systems and methods disclosed herein permit detection of injury by, among other things, facilitating communication between two sensors when an anatomic structure between the sensors is compromised.

In an embodiment, a system for evaluating the integrity of an anatomic structure may include a first sensor disposable through a first space on a first side of the anatomic structure, a second sensor disposed in a second space on a second side of the anatomic structure, and a processor coupled to the first sensor and to the second sensor, the processor including a meter, the meter responsive to a communication between the first sensor and the second sensor, wherein an invasion of the anatomic structure by the first sensor alters the communication between the first sensor and the second sensor.

In an embodiment, an electrical tissue injury detection system can include a first conductor disposable through a first space on a first side of an anatomic structure, a second conductor disposed in a second space on a second side of the anatomic structure, a conductive medium instilled into the second space and in communication with the second conductor, and a processor coupled to the first sensor and to the second sensor, the processor including a meter, the meter responsive to an electrical parameter between the first conductor and the second conductor.

In an embodiment, a kit for minimally invasive surgery can include a sling system, including a length of supporting material having a needle removably attached to an end thereof, and a catheter conductor, and an electrical tissue injury detection system, including the needle as a first conductor disposable through a first space on a first side of an anatomic structure, the catheter conductor as a second conductor disposed in a second space on a second side of the anatomic structure, a conductive medium instilled into the second space and in communication with the second conductor, and a processor coupled to the first sensor and to the second sensor, the processor including a meter, the meter responsive to an electrical parameter between the first conductor and the second conductor. In an embodiment, supporting material can include sling material. In an embodiment, supporting material can include tension-free vaginal tape. In an embodiment, supporting material can include synthetic and/or natural graft material commonly employed in suburethral sling surgery and/or antiincontinence surgery more generally. In an embodiment, supporting material can include a wide variety of materials used in surgical and medical procedures, such as meshes, filters, sutures, hemostats, and other materials and configurations known in the art.

In an embodiment, a method for detecting tissue injury can include placing a first sensor in a first space on a first side of an anatomic structure, placing a second sensor in a second space on a second side of an anatomic structure, and measuring a communication between the first sensor and the second sensor, wherein an invasion of the anatomic structure by the first sensor alters the communication between the first sensor and the second sensor.

An embodiment can include a conductive medium instilled into the second space and coupled to the second sensor. In an embodiment, the conductive medium can coat the second side of the anatomic structure. In an embodiment, the processor can provide an output signal indicative of the integrity of the anatomic structure.

In an embodiment, the first sensor can include a surgical tool. In an embodiment, the surgical tool can include a needle attached to a length of tension-free vaginal tape. In an embodiment, the second sensor can include a catheter conductor. In an embodiment, the catheter conductor can include at least one of a Foley catheter and a catheter guide.

In an embodiment, the first sensor and the second sensor can be coupled electrically to the processor, and the communication between the first sensor and the second sensor can include an electrical conduction. In an embodiment, the meter can include an ammeter. In an embodiment, the meter can include a voltmeter. In an embodiment, the meter can include a resistometer. In an embodiment, the meter can include an electrical conductometer.

In an embodiment, the anatomic structure can include a wall of a urinary bladder. In an embodiment, the first space can include the Space of Retzius. In an embodiment, the second space can include a lumen of the urinary bladder. In an embodiment, the second space can include a lumen of a vessel, such as a blood vessel, a lymph vessel, a cerebrospinal fluid vessel or space, a urinary vessel, a seminiferous vessel, or an airway vessel or passage. In an embodiment, the second space can include a lumen of a viscus. In an embodiment, the second space can include a lumen of a hollow organ.

An embodiment can include a power source. In an embodiment, the power source can provide power to the processor. In an embodiment, the power source can provide power to the first sensor. In an embodiment, the power source can provide power to the second sensor. In an embodiment, the power source can include a battery.

In an embodiment, at least one component of the system can be disposable. In an embodiment, at least one component of the system can be reusable.

BRIEF DESCRIPTION OF THE DRAWINGS

These and other features and advantages of the systems and methods disclosed herein will be more fully understood by reference to the following detailed description in conjunction with the attached drawings in which like reference numerals refer to like elements through the different views. The drawings illustrate principles of the systems and methods disclosed herein and are not necessarily to scale. Implied absolute or relative dimensions are not limiting but are instead provided for illustrative purposes.

DETAILED DESCRIPTION

The present disclosure describes, among other things, systems and methods used for the detection and/or measurement of electrical properties in a circuit to assess tissue injury or risk of injury during a surgical or other procedure. In particular, systems and methods are described for monitoring the occurrence of bladder injury during antiincontinence surgery.

Figure 1:
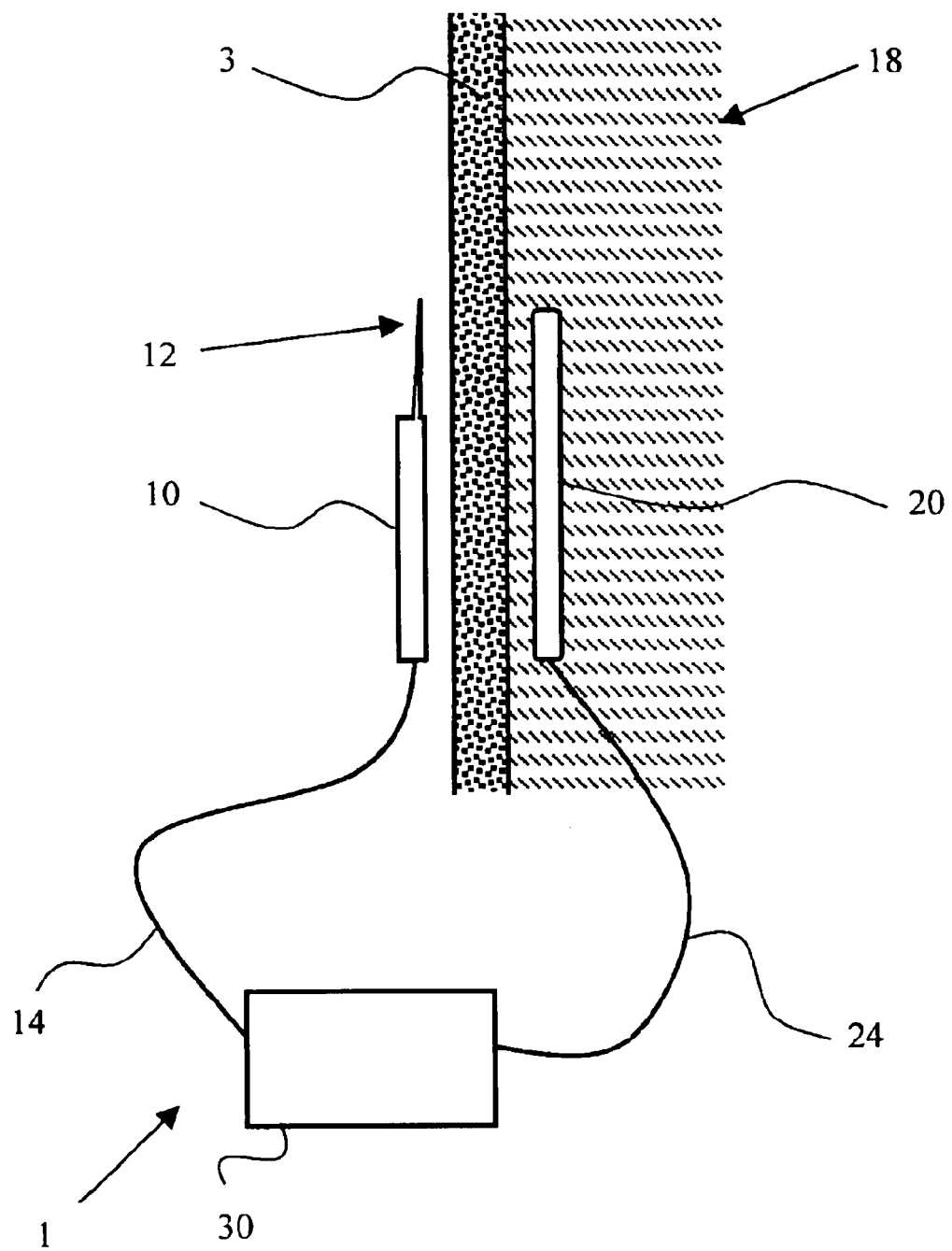
FIGS. 1–6 depict schematically embodiments of disclosed systems and methods.

FIG. 1 depicts an exemplary schematic of a device according to an embodiment. A monitoring system 1 can include a first sensor 10 and a second sensor 20. The sensors may be placed on alternate sides of an anatomic structure 3. The first sensor 10 and the second sensor 20 may be coupled to a processor 30 by connections 14, 24, respectively. The sensors 10, 20, the connections 14, 24, and the processor 30 may form an open circuit conduction pathway. A source of power or other communication medium to the circuit may be provided, such as from a battery, a light source, a sound source, or by a connection to another electrical circuit (not shown). To facilitate communication to and/or from the second sensor 20, a conduction medium 18 may be provided. In an embodiment, the first sensor 10 can include a tool, such as a surgical tool, and may include a piercing tip 12. A wide variety of surgical tools are known in the art, including but not limited to scalpels, scissors, forceps, needles, trocars, introducers, specula, intravascular lines, guidewires, catheters, syringes, and others.

In operation, a device according to the exemplary embodiment can be used to evaluate the integrity of an anatomic structure, such as schematically represented anatomic structure 3. Integrity can be, for example,.the completeness of the barrier provided by the structure. The first sensor 10 can be positioned in a space on a first side of the anatomic structure 3. The first sensor 10 can be disposable through the space. For example, the first sensor 10 can be disposed temporarily or transiently in the space while being moved through the space. The second sensor 20 can be disposed in a second space on a second side of the anatomic structure 3. In an embodiment, the first side and second side can be opposite surfaces of the anatomic structure 3. In an embodiment, one side can be an outer surface, and the other side can be an inner surface of a lumen, a vessel, and/or a hollow-walled organ.

With elements of the system 1 positioned as shown schematically in FIG. 1 (i.e., with the first sensor 10 not contacting the anatomic structure 3), and the integrity of the structure is intact, there is no, minimal, or low communication (collectively, henceforth, "low signal") between the first sensor 10 and the second sensor 20. In an embodiment, there is an open or near-open circuit between the sensors 10, 20 and therefore little electrical conduction. The low signal between the sensors may be detected by the processor 30. In an embodiment, a low signal may be interpreted by the processor 30 as an indication that the anatomic structure has not been contacted by the first sensor 10. The sensor 30 may provide an output (not shown) that indicates the non-contact, or "Normal" condition. The output may be provided in a variety of embodiments, such as an audible or visible indicator, or as an electrical or electronic signal to another device. The Normal condition output could also be provided as the absence of or interruption of an audible, visible, or other signal. The Normal condition signal can be interpreted by, for example, a user of the device to indicate that the integrity of the anatomic structure being studied is intact.

A wide variety of paradigms may permit communication between the sensors 10, 20. For example, the sensors may include electrical conductors, and a low signal would result when there is little or no current flow or high electrical resistance in the path between the sensors. Thus, an intact anatomic structure 3 could provide a substantial electrical barrier to conduction between the sensors. Thus, a low signal would indicate that the anatomic structure 3 was not contact by one or both sensors. In contrast, substantial electrical conduction could result if the first sensor 10 contacts, pierces, or penetrates the anatomic structure 3, as described below. The conduction medium 18 can include electrolytes to facilitate conduction from and/or to the second conductor.

Other communication paradigms are contemplated. For example, the sensors 10, 20 could include light sources and/or light receivers. In an embodiment, the first sensor 10 could emit light, while the second sensor 20 could receive light. While the sensors are separated by the anatomic structure 3, little or no light could be detected by the second sensor 20. The sensor 30 could interpret the lack or paucity of light reception as a low signal and provide an appropriate output. Analogously, the first sensor 10 could emit other types of electromagnetic energy, and the second sensor 20 could detect the electromagnetic energy. The first sensor 10 could emit laser light, and the second sensor 20 could receive laser light. The first sensor 10 could emit sound energy, and the second sensor 20 could receive sound energy. The first sensor 10 could emit a tracer, such as a dye, and the second sensor 20 could detect the tracer or dye. The dye could be a fluorescent dye. The dye could be a blue dye. The first and second sensors 10, 20 could perform opposite roles. In an embodiment, the conduction medium 18 can facilitate light transmission, for example, by facilitating coherent or focused light transmission. In an embodiment, the conduction medium 18 can facilitate sound transmission, for example, by providing a fluid medium to promote propagation of pressure waves between the sensors.

The connections 14, 24 can facilitate transmission of signals to the processor 30. The connections can include a wire to support electrical transmission. A wide variety of electrical couplings are contemplated. The connections can include radiofrequency or other electromagnetic energy transmitters and/or receivers. The connections can be wireless. The connections can form a network including the sensors 10, 20 and the processor 30. The connections can include an optical transmission pathway, such as an optical fiber. The connections can include a fluid column to conduct sound or pressure signals.

Figure 2:
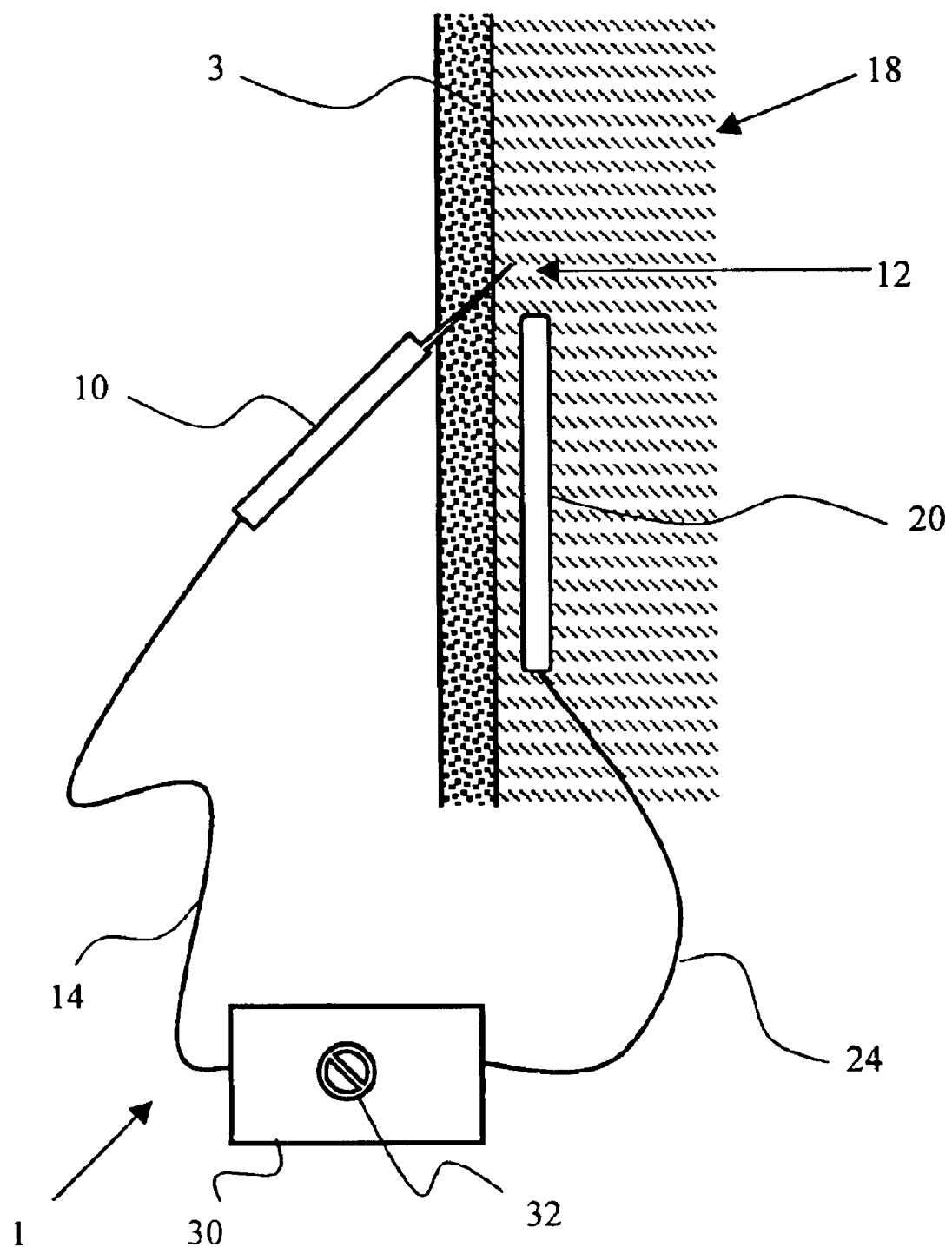

FIG. 2 schematically depicts the monitoring system 1 wherein the first sensor 10 has invaded or penetrated the anatomic structure 3. Invasion can include but is not limited to contacting, piercing, penetrating, perforating, grazing, and/or abrading the structure, as well as other interactions that can damage or perturb the structure, as are known in the art. Invasion and other causes of loss of integrity in the anatomic structure 3 can result in an alteration of the communication between the sensors 10, 20.

As depicted in FIG. 2, the first sensor 10 and the second sensor 20 may communicate through the conduction medium 18. Impedance of communication caused by the anatomic structure 3 can be diminished because it no longer provides a barrier to communication between the sensors. For example, if the communication occurs by electrical transmission, then an electrical circuit may be completed between the sensors by a conduction medium 18 that can support electrical conduction, as described elsewhere in this disclosure. Analogously, penetration of a sensor through the anatomic structure 3 may create a light path or other electromagnetic conduit between the sensors, or a path for sound to travel with diminished damping caused, e.g., by the anatomic structure 3. This can result in a high signal being communicated between the sensors.

The first sensor 10 need not penetrate fully through the anatomic structure 3. The first sensor 10 can create a communication and/or conduction pathway through the anatomic structure 3, such as by creating a defect or aperture in the structure through which an electrical signal may propagate. The first sensor 10 could also create a defect or aperture in the structure 3 that could facilitate communication of a light or other electromagnetic radiation signal between the sensors. Analogously, the first sensor 10 could create a defect or aperture through which a sound signal could be communicated between the sensors.

Communication between the sensors above that for a low signal may be interpreted by the sensor 30 as a high signal. In an embodiment, there is a short- or near-short circuit between the sensors 10, 20 and therefore much electrical conduction. In an embodiment, there is a closed circuit between the sensors 10, 20, and therefore electrical conduction. The high signal between the sensors may be detected by the processor 30. In an embodiment, a high signal may be interpreted by the processor 30 as an indication that the anatomic structure has been contacted, pierced, and/or penetrated by the first sensor 10. The sensor 30 may provide an output 32 that indicates the contact, piercing, and/or penetration, or "Abnormal" condition. The abnormal condition output 32 may be provided in a variety of embodiments, such as an audible or visible indicator, or as an electrical or electronic signal to another device. The abnormal condition output 32 could also be provided as the absence of or interruption of an audible, visible, or other signal.

Figure 3:
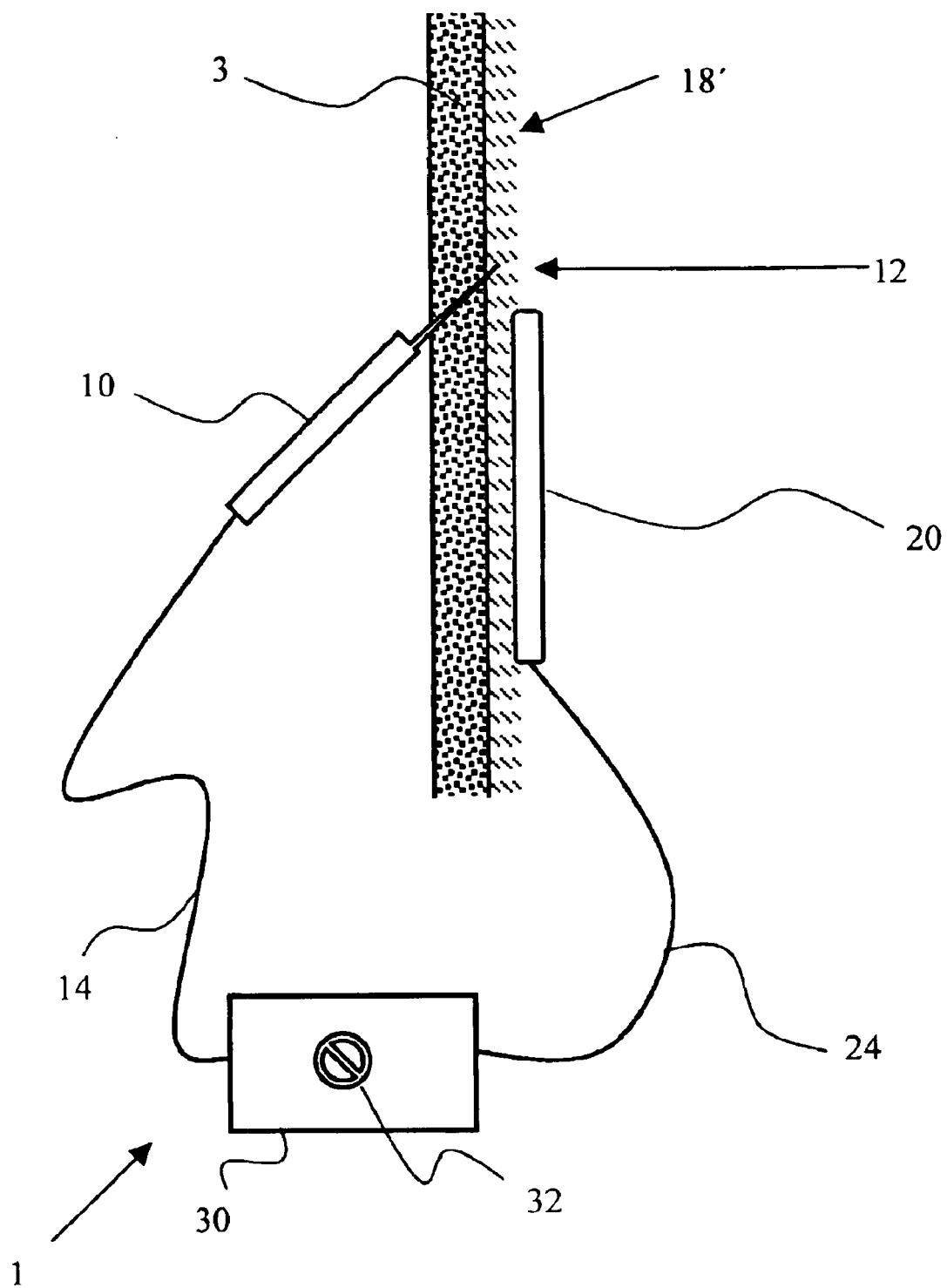

FIG. 3 schematically depicts an embodiment in which a surface conduction medium 18' is provided as a coating on a side of the anatomic structure 3. The surface conduction medium 18' can share properties of conduction medium 18. Surface conduction medium 18' can be viscid. It can be adapted to adhere to a surface. It can be adapted to cling to a surface. As depicted in FIG. 3, sufficient surface conduction medium 18' can be provided to facilitate communication between sensors 10, 20 should the first sensor 10 contact, piece, and/or penetrate the anatomic structure 3. For example, anatomic structure 3 could define the wall of a lumen or hollow viscus. In an embodiment, the amount of surface conduction medium 18' to coat a surface of the anatomic structure 3 can be less than the amount of another conduction medium, which may have to be provided in sufficient quantity to fill or to partially fill the lumen. A smaller amount of conduction medium may be easier or cheaper to instill than a larger amount.

Figure 4:
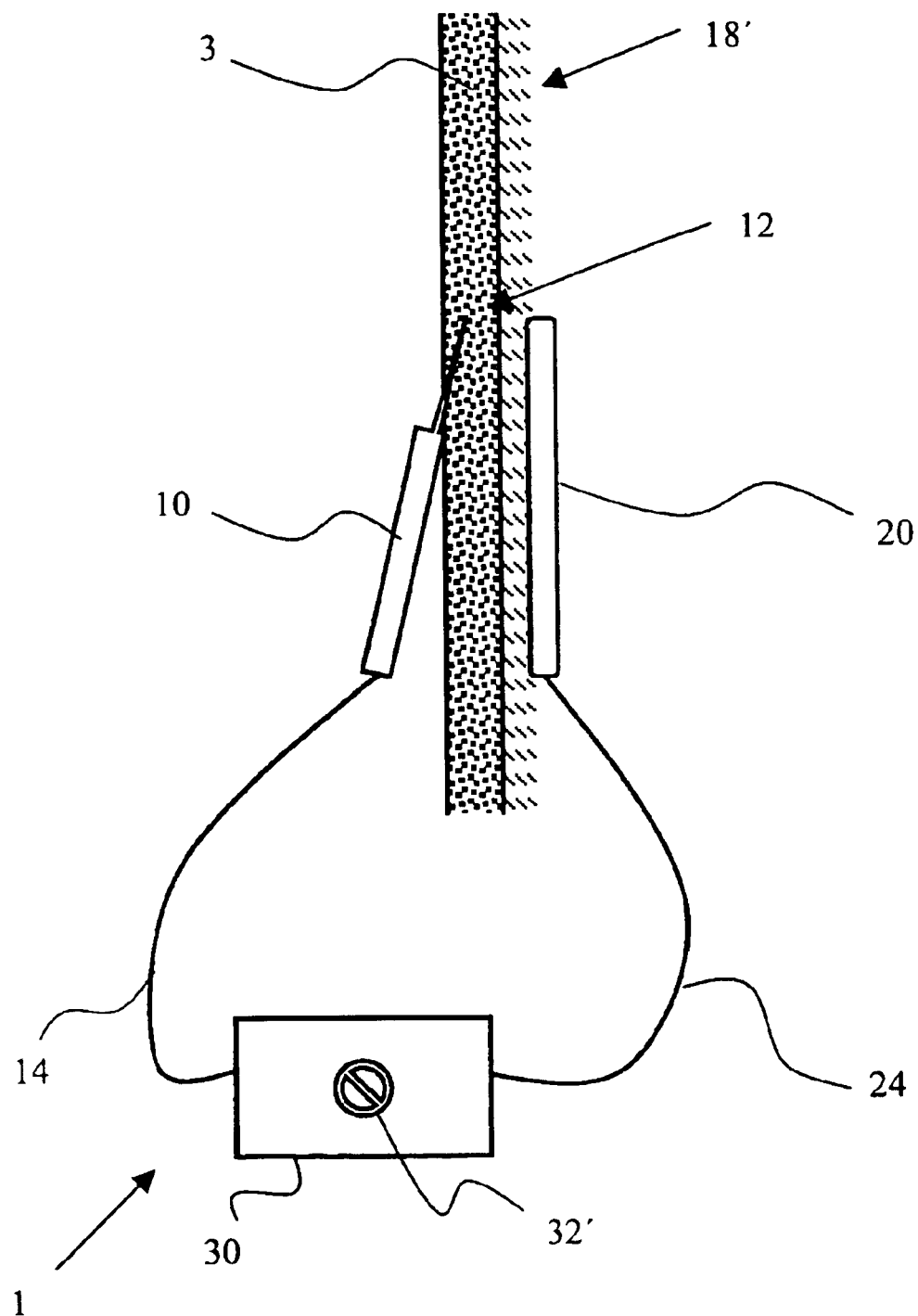

FIG. 4 schematically depicts the monitoring system 1 wherein the first sensor 10 has pierced or partially penetrated the anatomic structure 3. Although the first sensor 10 need not fully penetrated the anatomic structure 3, it can penetrate a sufficient portion of the structure to increase measurably the amount of communication that can pass between the sensors as compared to the condition schematically depicted in FIG. 1, in which a low signal can be communicated. The amount of communication between the sensors in the condition depicted in FIG. 4 can be a high signal. The amount of communication between the sensors in the condition depicted in FIG. 4 could be an intermediate signal, between the low signal and the high signal. The magnitude of the intermediate signal could be interpreted by the processor 30 to represent the degree of invasion of the first sensor 10 onto or into the anatomic structure 3. For example, if the first sensor contacts a surface of the anatomic structure 3, then the anatomic structure could still provide most of the impedance that it could when the first sensor 30 is not contacting the anatomic structure 3. However, as the first sensor penetrates the anatomic structure 3, a decreasing thickness of the structure can be available to provide impedance to communication between the sensors. In response to an intermediate signal, the processor 30 can provide an output signal 32' that indicates the contact, piercing, and/or partial penetration, or "Warning" condition. The processor can also produce an "Abnormal" condition signal. The warning condition output 32' may be provided in a variety of embodiments, such as an audible or visible indicator, or as an electrical or electronic signal to another device. The warning condition output 32' could also be provided as the absence of or interruption of an audible, visible, or other signal.

EXAMPLE

Figure 5:
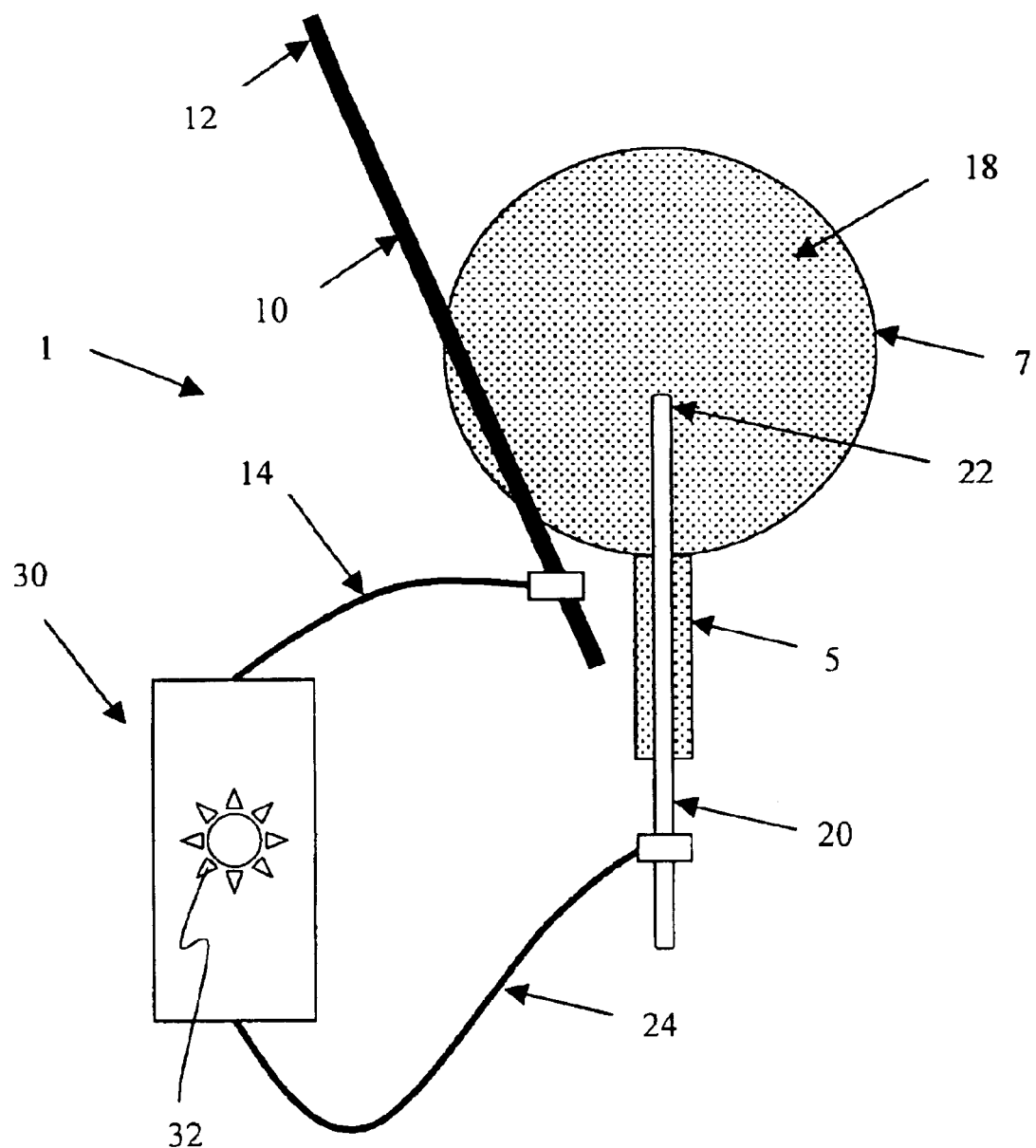

FIG. 5 shows an embodiment of a monitoring system 1 employed as a bladder injury detection system. The system 1 can include a processor 30 with an electrical device that can provide a source of electricity (e.g., current or voltage) through the circuit created by an introducer needle 10, a catheter conductor 20, and the conductive fluid 18 in the bladder 7. The catheter conductor 20 can include, for example, a rigid catheter guide. The catheter conductor 20 can include a catheter with electrical conduction properties. The catheter conductor 20 can include an electrode applied to a catheter and/or to a catheter guide. Connections 14, 24 can be provided to connect the needle 10 and the catheter conductor 20 to the processor 30, respectively. A catheter 22 can be provided with a conductor (not shown) and connected to the connection 24 instead of providing a catheter guide as the second sensor 20. The processor 30 can include an electrical meter, such as an ammeter, a voltmeter, a resistometer, and/or an electrical conductometer, as known and described in the art. The electrical meter can measure an electrical parameter to characterize the electrical communication between the needle 10 and the guide 20 and thereby determine whether a bladder injury has occurred. For example, if the needle 10 contacts, pierces, grazes, penetrates, and/or, as depicted in FIG. 5, skewers the bladder 7, an increase in current may be measured by the electrical meter as compared to the uninjured state. A decrease in resistance may be measured. A decrease in voltage may be measured. An increase in conductance may be measured. The processor can produce an output signal 32, such as an alarm, when a change in an electrical property indicative of an injury has occurred.

Figure 6:
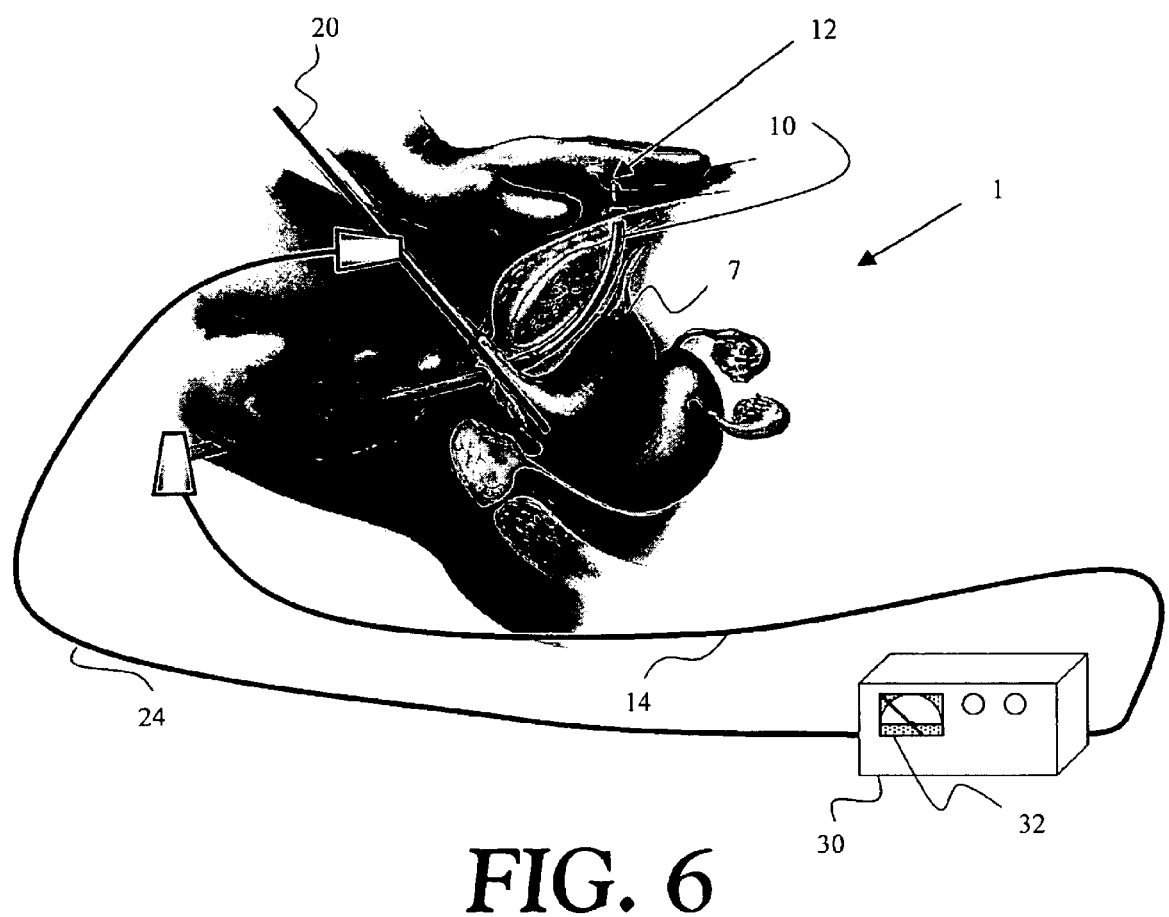

FIG. 6 shows the system in a TVT procedure. In a TVT procedure, a length of tension-free vaginal tape (not shown) is provided with a needle 10 disposed on one or both ends of the tape. The needle 10 is advanced paravaginally through the retropubic space to an abdominal incision. The tape can be slung under the urethra and its ends affixed to anatomic features such as abdominal muscle or fascia, with the needles removed. This procedure can treat disorders such as stress urinary incontinence due to, for example, urethral hypernobility and/or intrinsic sphincter deficiency.

As the needle 10 is placed up through the retropubic space, it can be mistakenly advanced into, onto, or near the wall of the bladder 7. Since the wall of the bladder 7 is primarily muscular, it is susceptible to injury by sharp objects such as the piercing tip 12 of the needle 10. During and/or after insertion of the needle 10, the monitoring system 1 can be employed to monitor or test whether bladder injury has occurred.

In one embodiment, two conductors are used, one placed in the Space of Retzius and one placed in the bladder. In certain embodiments, a metallic needle 10 may be used as one conductor, and a conductive device 20 incorporated in a Foley catheter may be used as the other. After passing the metallic needle 10 paravaginally or suprapubically into the Space of Retzius, the bladder 7 can be filled in a retrograde fashion though a Foley catheter with a quantity of a conducting distention fluid (not shown), such as normal or hypertonic saline. A volume of about 300 cc may be preferred, but volumes of a reasonable amount to fill or partially fill a bladder can be employed. A source of electricity 30 is attached to the catheter conductor 20 or the metallic needle 10 to provide electrical impulses thereto. If the needle 10 has penetrated the bladder 7, a circuit will be created wherein an electrical parameter may be measured, as described above. In an embodiment, current will be high and resistance will be minimal when an injury has occurred. Alternatively, if the needle 10 has not entered the bladder 7, the resistance provided by the bladder wall will prevent or substantially prevent the circuit from being created. With the application of a source of electricity to either the catheter or the needle, no or little current will be detected. With direct current, it is known that Voltage=Current×Resistance. An electrical device may provide a current or a voltage across the circuit. For example, a voltage may be applied to the circuit (e.g. battery) and the current may be measured with an ammeter. In this manner, the resistance can be easily calculated, to determine whether or not the needle has injured the bladder. Alternatively, one may put out a fixed current and measure voltage, to determine resistance. The current measured would depend on the resistance in the tissues. For example, saline has a very low resistance, while the resistance would be higher through the bladder wall. The differences in resistance would be used to differentiate between a needle placed through the bladder and a properly placed needle.

If this kind of bladder injury has occurred, the needle 10 may be withdrawn and replaced after emptying the bladder 7. The procedure could then be repeated to rule out a second injury. Alternatively, cystoscopy could be recommended to rule out a second injury (which would occur in a small minority of patients), since fluid may leak out of the original hole and make contact with a properly placed needle. Such an occurrence may lead to a false positive reading on the ammeter, suggesting to the surgeon that the needle should be replaced once again, when, in fact, the needle is in the correct position. For this reason, the second placement after a confirmed bladder injury may preferably be directly observed with cystoscopy.

This concept may also be used to prevent or reduce the extent of a needle injury. If the needle is placed with a minimal amount of conductive fluid in the bladder (approximately 50 cc), this device could indicate early perforation of the bladder lining, limiting the injury to a small puncture site. The operator could then back up and redirect the needle in the proper position. Alternatively, rather than using a standard saline solution, a viscous saline solution such as a saline-hyskon solution could be used to coat the bladder wall, which may improve the conduction in the bladder while permitting only a minimal amount of fluid to be introduced in the bladder. This would reduce the likelihood of bladder injury by lowering the volume of fluid needed in the bladder during needle passage.

Alternatively, the resistance of the bladder wall may permit some reduced but predictable conduction through the wall to the introducer needle, in effect warning the surgeon when the needle has approached close to, but not through, the bladder wall. This would, again, permit the surgeon to redirect the needle in order to prevent bladder injury.

In an embodiment, the electrical device can put out a fixed voltage, an ammeter that measures current through the circuit, and the disposable wires that would connect to the introducer needle and rigid catheter guide.

In an embodiment, a monitoring system could be provided with a TVT kit. The kit could include a length of TVT with a needle attached to one or both ends, a catheter guide and/or a Foley catheter, connections, and a processor. The connections could include clips for simple attachment and detachment from the needle, the guide or catheter, and/or the processor. The connection wires could be embedded in the TVT. The processor could be battery powered. The processor could be incorporated in the first sensor. The processor could be incorporated or in the second sensor. The processor could be disposable. The processor could be reusable.

In an embodiment, a monitoring system can be employed for electrical detection of bladder injuries during open or laparoscopic surgery that involves structures adjacent to the bladder or ureters. For example, during open laparoscopic bladder neck suspension (Burch procedure), sutures are placed in the endopelvic fascia near the urethra and bladder. In this situation, one sensor would be the needle driver holding the needle (with suture attached), and the other sensor would be the metal catheter guide in the Foley catheter. If the needle inadvertently penetrates the bladder during surgery, the surgeon would be alerted immediately that the bladder has been violated, and the needle may be withdrawn and replaced in an appropriate location.

Electrical detection of surgical injuries could be applied to other cavities in the body where fluid may be placed to act as conductive media, so that inadvertent injury by needles of sutures can be prevented or detected. Such principles may be applied to gastrointestinal surgery, including the esophagus, stomach, small and large intestines, and/or rectum. Similarly, surgery on the upper urinary tract could employ this technology to prevent injury to the renal calyxes and/or ureters. In addition, urologic surgery performed near the bladder (such as prostatectomy) could use this technology to prevent placement of permanent sutures in the bladder. In other gynecologic applications, transvaginal surgery may use these techniques to prevent inadvertent bladder injury. For example, transvaginal paravaginal repair of cystoceles may employ techniques that involve suturing or other devices placed directly through the mucosa to reapproximate the endopelvic fascia to the pelvic sidewall. A system as described above that detects bladder injury could direct the surgeon to safe areas for appropriate tissue apposition.

While the systems and methods disclosed herein have been particularly shown and described with references to exemplary embodiments thereof, it will be understood by those skilled in the art that various changes in form and details may be made therein without departing from the spirit and scope of the disclosure. Those skilled in the art will recognize or be able to ascertain using no more than routine experimentation, many equivalents to the exemplary embodiments described specifically herein. Such equivalents are intended to be encompassed in the scope of the present disclosure.

What is claimed is:

1. A system for evaluating the integrity of an anatomic structure, comprising:
    a first sensor component comprising a surgical tool including a needle, the tool being attached to a length of supporting material, the first sensor component being disposable though a first space on a first side of the anatomic structure;
    a second sensor component disposable in a second space on a second side of the anatomic structure; and
    a processor coupled to the first sensor component and to the second sensor component the processor including a meter, the meter responsive to a communication between the first sensor component and the second sensor component;
    wherein an invasion of the anatomic structure by the first sensor component alters the communication between the first sensor component and the second sensor component.

2. The system of claim 1, further comprising a conductive medium adapted to be instilled into the second space and coupled to the second sensor component.

3. The system of claim 2, wherein the conductive medium is adapted to coat the second side of the anatomic structure.

4. The system of claim 1, wherein the processor provides an output signal indicative of the integrity of the anatomic structure.

5. The system of claim 1, wherein the second sensor component comprises a catheter conductor.

6. The system of claim 5, wherein the catheter conductor comprises at least one of a Foley catheter and a catheter guide.

7. The system of claim 1, wherein the first sensor component and the second sensor component are coupled electrically to the processor, and the communication between the first sensor component and the second sensor component comprises an electrical conduction.

8. The system of claim 7, wherein the meter comprises at least one of an ammeter, a voltmeter, a resistometer, and an electrical conductometer.

9. The system of claim 1, wherein the atomic structure comprises a wall of a urinary bladder, the first space comprises the Space of Retzius, and the second space comprises a lumen of the urinary bladder.

10. The system of claim 1, further comprising a power source providing power to at least one of the processor, the first sensor component and the second sensor component.

11. The system of claim 10, wherein the power source comprises a battery.

12. The system of claim 1, wherein at least one part of the system is disposable.

13. The system of claim 1, wherein at least one part of the system is reusable.

14. An electrical tissue injury detection system, comprising:
    a first conductor comprising a surgical tool including a needle, the tool being attached to a length of of supporting material, the first conductor being disposable through a first space on a first side of an anatomic structure;
    a second conductor disposable in a second space on a second side of the anatomic structure;
    a conductive medium adapted to be instilled into the second space and in communication with the second conductor; and
    a processor coupled to the first conductor and to the second conductor, the processor including a meter, the meter responsive to an electrical parameter between the first conductor and the second conductor.

15. A kit for minimally invasive surgery, comprising:
    a sling system, including:
        a length of supporting material having a needle removably attached to an end thereof; and
        a catheter conductor; and
    an electrical tissue injury detection system, including:
        the needle as a first conductor disposable through a first space on a first side of an anatomic structure;
        the catheter conductor as a second conductor disposable in a second space on a second side of the anatomic structure;
        a conductive medium adapted to be instilled into the second space and in communication with the second conductor; and
        a processor coupled to the first conductor and to the second conductor, the processor including a meter, the meter responsive to an electrical parameter between the fist conductor and the second conductor.

16. A method for detecting tissue injury, comprising:
    placing a first sensor component in a first space on a first side of an anatomic structure, the first sensor component comprising a surgical tool including a needle, the tool being attached to a length of supporting material;
    placing a second sensor component in a second space on a second side of an anatomic structure; and
    measuring a communication between the first sensor component and the second sensor component;
    wherein an invasion of the anatomic structure by the first sensor component alters the communication between the first sensor component and the second sensor component.

17. The method of claim 16, further comprising instilling a conductive medium in the second space.

18. The method of claim 16, wherein the first sensor component comprises a first conductor, the second sensor component comprises a second conductor, and measuring comprises measuring an electrical parameter between the first conductor and the second conductor.

19. A method for detecting tissue injury, comprising:
placing a first sensor component in a first space on a first side of an anatomic structure, the first sensor component comprising a surgical tool including a needle;
attaching the surgical tool to a length of supporting material;
placing a second sensor component in a second space on a second side of an anatomic structure; and
measuring a communication between the first sensor component and the second sensor component;
wherein an invasion of the anatomic structure by the first sensor component alters the communication between the first sensor component and the second sensor component.

20. A system for evaluating the integrity of a wall of a urinary bladder, comprising:
a first sensor component disposable through the Space of Retzius on a first side of the wall of the urinary bladder;
a second sensor component disposable in a lumen of the urinary bladder on a second side of the wall of the urinary bladder; and
a processor coupled to the first sensor component and to the second sensor component, the processor including a meter, the meter responsive to
a communication between the first sensor component and the second sensor component;
wherein an invasion of the wall of the urinary bladder by the first sensor component alters the communication between the first sensor component and the second sensor component.

21. The system of claim 20, further comprising a conductive medium adapted to be instilled into the lumen of the urinary bladder and coupled to the second sensor component.

22. The system of claim 21, wherein the conductive medium is adapted to coat the second side of the wall of the urinary bladder.

23. The system of claim 20, wherein the processor provides an output signal indicative of the integrity of the anatomic structure.

24. The system of claim 20, wherein the second sensor component comprises a catheter conductor.

25. The system of claim 24, wherein the catheter conductor comprises at least one of a Poley catheter and a catheter guide.

26. The system of claim 20, wherein the fist sensor component and the second sensor component are coupled electrically to the processor, and the communication between the first sensor component and the second sensor component comprises an electrical conduction.

27. The system of claim 26, wherein the meter comprises at least one of an ammeter, a voltmeter, a resistometer, and an electrical conductometer.

28. The system of claim 20, further comprising a power source providing power to at least one of the processor, the first sensor component, and the second sensor component.

29. The system of claim 28, wherein the power source comprises a battery.

30. The system of claim 20, wherein at least one part of the system is disposable.

31. The system of claim 20, wherein at least one part of the system is reusable.

32. A system for evaluating the integrity of an anatomic structure, comprising:
a first sensor component comprising a surgical tool including a piercing tip, the tool being attached to a length of supporting material, the first sensor component being disposable through a first space on a first side of the anatomic structure;
a second sensor component disposable in a second space on a second side of the anatomic structure; and
a processor coupled to the first sensor component and to the second sensor component, the processor including a meter, the meter responsive to a communication between the first sensor component and the second sensor component;
wherein an invasion of the anatomic structure by the first sensor component alters the communication between the first sensor component and the second sensor component.

33. The system of claim 32, wherein the anatomic structure comprises a wall of a urinary bladder, the first space comprises the Space of Retzius, and the second space comprises a lumen of the bladder.

34. A kit for minimally invasive surgery, comprising:
a sling system, including:
a length of supporting material; and
a catheter conductor; and
an electrical tissue injury detection system, including:
the needle as a first conductor disposable through a first space on a first side of an anatomic structure, the needle being removably attachable to an end of the supporting material;
the catheter conductor as a second conductor disposable in a second space on a second side of the anatomic structure;
a conductive medium adapted to be instilled into the second space and in communication with the second conductor; and
a processor coupled to the first conductor and to the second conductor, the processor including a meter, the meter responsive to an electrical parameter between the first conductor and the second conductor.

* * * * *